(12) United States Patent
Connell et al.

(10) Patent No.: US 12,072,306 B2
(45) Date of Patent: Aug. 27, 2024

(54) METHOD AND SYSTEM FOR HIGH SPEED DETECTION OF DIAMONDS

(71) Applicant: University of Johannesburg, Johannesburg (ZA)

(72) Inventors: Simon H. Connell, Johannesburg (ZA); Martin N. Cook, Johannesburg (ZA); Richard C. Andrew, Johannesburg (ZA)

(73) Assignee: University of Johannesburg, Johannesburg (ZA)

( * ) Notice: Subject to any disclaimer, the term of this patent is extended or adjusted under 35 U.S.C. 154(b) by 659 days.

(21) Appl. No.: 17/292,385

(22) PCT Filed: Nov. 8, 2019

(86) PCT No.: PCT/IB2019/059615
§ 371 (c)(1),
(2) Date: May 7, 2021

(87) PCT Pub. No.: WO2020/095263
PCT Pub. Date: May 14, 2020

(65) Prior Publication Data
US 2021/0293729 A1    Sep. 23, 2021

(30) Foreign Application Priority Data
Nov. 8, 2018   (NL) ..................... 2021956

(51) Int. Cl.
*G01N 23/221*   (2006.01)
*B07C 5/346*    (2006.01)
*G01N 33/38*    (2006.01)

(52) U.S. Cl.
CPC .......... *G01N 23/221* (2013.01); *B07C 5/346* (2013.01); *G01N 33/381* (2013.01); *G01N 2223/074* (2013.01); *G01N 2223/60* (2013.01)

(58) Field of Classification Search
None
See application file for complete search history.

(56) References Cited

U.S. PATENT DOCUMENTS 6,563,123 B1 * 5/2003 Sellschop ............... G21G 1/12
                                                    977/901
8,884,251 B2 * 11/2014 Twitchen .............. C01B 32/28
                                                    250/492.1

(Continued)

FOREIGN PATENT DOCUMENTS

WO    WO-2018/200493 A1    11/2018
WO    WO-2020261145 A1 *  12/2020 ........... G06T 11/005

OTHER PUBLICATIONS

Breeding et al. (The "Type" Classification System of Diamonds and Its Importance in Gemology; "Type" Classification of Diamonds; Gems & Gemology;Summer 2009; pp. 96-111) (Year: 2009).*

(Continued)

*Primary Examiner* — David P Porta
*Assistant Examiner* — Djura Malevic
(74) *Attorney, Agent, or Firm* — Dana M. Gordon; Stephen J. Kenny; Foley Hoag LLP

(57) ABSTRACT

THIS INVENTION relates to a method of or system for detecting presence of diamond in an object. The method comprises receiving classification data associated with photons emitted from object as a result of positron annihilation due to irradiation of the object with photons of a predetermined energy at which giant dipole resonance (GDR) occurs due to a nuclear reaction between the photons and carbon. The method then comprises the step of determining whether or not the object is potentially a diamond or diamondiferous by processing the received classification data with a trained machine-based learning classifier. The system typically implements the method described herein.

20 Claims, 7 Drawing Sheets

(56) References Cited

U.S. PATENT DOCUMENTS

| | | | | |
|---|---|---|---|---|
| 8,884,252 | B2* | 11/2014 | Twitchen | B24D 99/00 250/492.1 |
| 8,890,091 | B2* | 11/2014 | Twitchen | C09K 3/1409 250/492.1 |
| 11,543,360 | B2* | 1/2023 | Raichelgauz | G06V 10/421 |
| 2010/0329965 | A1* | 12/2010 | Twitchen | C23C 16/277 117/88 |
| 2013/0205680 | A1* | 8/2013 | Twitchen | C30B 33/04 51/307 |
| 2013/0334429 | A1* | 12/2013 | Fukuchi | G06T 7/0012 250/363.03 |
| 2014/0294147 | A1* | 10/2014 | Chen | G01V 5/0066 378/57 |
| 2020/0241164 | A1* | 7/2020 | Connell | G01V 5/12 |
| 2020/0405821 | A1* | 12/2020 | Kumar | A61L 27/18 |
| 2021/0003510 | A1* | 1/2021 | Raichelgauz | B07B 13/003 |
| 2021/0293729 | A1* | 9/2021 | Connell | G01N 33/24 |
| 2022/0057344 | A1* | 2/2022 | Connell | G01T 1/2985 |
| 2022/0215520 | A1* | 7/2022 | Parikh | G06V 20/20 |
| 2022/0358693 | A1* | 11/2022 | Connell | G06T 7/0004 |

OTHER PUBLICATIONS

Ballesterro et al. (Mineral-PET: Kimberlite sorting by nuclear-medical technology; researchgate; 2010) (Year: 2010).*

Cook et al. (Overview of the Mineral-Pet run-of-mine Diamond bearing rock sorter; researchgate; 2014) (Year: 2014).*

Langs et al. (Machine learning: from radiomics to discovery and routine; Radiologe 2018 • 58 (Suppl 1):S1-S6; Jun. 19, 2018.*

Ballestrero et al. (Mineral-PET: Kimberlite sorting by nuclear-medical technology; Sergio Ballestrero University of Johannesburg, pp. 589-602).*

Ballestrero et al., "Mineral-PET: Kimberlite sorting by nuclear-medical technology," 12th International Conference on Nuclear Reaction Mechanisms, pp. 589-602 (2010).

Chinaka, "Radiation shielding analysis and optimisation for the mineral-PET Kimberlite sorting facility using the Monte Carlo calculation code MCNPX," Thesis submitted to the Faculty of Science, University of Johannesburg, Johannesburg, in fulfillment of the requirements for the degree of Master of Philosophy (2014).

Connell et al., "Discovering diamonds," CERN Courier, 57(6): 29-32 (2017).

Dimitrios, "Development of new machine learning methods for medical image processing and analysis," University of Patras School of Health Sciences Faculty of Medicine Interdepartmental Postgraduate Program in Medical Physics (2006).

Hidetaka et al., "Automated method for extraction of lung tumors using a machine learning classifier with knowledge of radiation oncologists on data sets of planning CT and FDG-PET/CT images," Engineering in Medicine and Biology Society (EMBC), 2013 35th Annual International Conference of the IEEE, pp. 2988-2991 (2013).

International Search Report for International Application No. PCT/IB2019/059615 dated Jan. 13, 2020.

Nemakhavhani et al., "The MinPET diamond discovery technique," Proceedings of the south African Institute of Physics of Conference 2017.

Arimura et al., "Automated method for extraction of lung tumors using a machine learning classifier with knowledge of radiation oncologists on data sets of planning CT and FDG-PET/CT images," Engineering in Medicine and Biology Society (EMBC), 2013 35th Annual International Conference of the IEEE, pp. 2988-2991 (2013).

* cited by examiner

METHOD AND SYSTEM FOR HIGH SPEED DETECTION OF DIAMONDS

This application is a national stage application filed under 35 U.S.C. § 371 of International Patent Application No. PCT/IB2019/059615 filed on Nov. 8, 2019 entitled METHOD AND SYSTEM FOR HIGH SPEED DETECTION OF DIAMONDS, which claims the benefit of Application 2021956 filed on Nov. 8, 2018 in the Netherlands. The entire contents of the above applications are incorporated herein by reference in their entirety.

FIELD OF INVENTION

THIS INVENTION relates to methods and systems for detection of diamonds in objects such as rocks, for example, kimberlite rocks.

BACKGROUND OF THE INVENTION

In conventional diamond mining operations, vast amounts of resources such as water and energy are required to process mostly barren rock in order to recover diamonds. Processing of the rock typically includes a very damaging sequence of rock crushing and diamond recovery often with a relatively low yield, for example, approximately 1 carat per ton of rock processed. However, crushing of rock in a conventional fashion may lead to diamond breakage reducing the profitability of a diamond mine.

Sensor based technologies attempt to negate these undesirable effects by enabling early detection of relatively unprocessed diamond bearing rocks which can then be isolated and processed in an environmentally friendly manner that preserves diamond integrity. However, sensor technology produces data which must be processed in complex ways to enhance the sensitivity and accuracy of the diamond detection. This processing makes use of complex algorithmic processes to achieve desired sensitivity at the cost of computational resources.

One prior art technology makes use of Positron Emission Tomography (PET) to be able to detect diamonds in rocks. This approach involves irradiating a rock with a gamma ray beam from bremsstrahlung of, for example, 40 MeV electrons, or a different source of photons other than bremsstrahlung, for example, inverse Compton scatter, or other techniques. The rock returns to moderate levels of specific activity within minutes, by which time the PET isotopes represent the dominant residual activity. When the $^{11}C$ pet isotope is the dominant activity, after about 30 minutes, the rock is then inspected by sensor arrangement to determine whether or not there is a diamond present therein. A problem with this prior art technology is that it is difficult to be able to inspect irradiated rocks at a high throughput with sensitivity which is acceptable and commercially viable in a mining environment where approximately 700 tons of rock is processed per hour. Moreover, it is desirable to detect diamonds or diamondiferous material within seconds for downstream ejection systems.

It is at least an object of the present invention to address the aforementioned problems and provide an alternate and improved means of detecting diamonds in rocks.

SUMMARY OF THE INVENTION

According to a first aspect of the invention, there is provided a method of detecting presence of diamond in an object, the method comprising:

receiving classification data associated with photons emitted from object as a result of positron annihilation due to irradiation of the object with photons of a predetermined energy at which giant dipole resonance (GDR) occurs due to a nuclear reaction between the photons and carbon, wherein the photons emitted are detected by a suitable detector arrangement; and determining whether or not the object is potentially a diamond or diamondiferous by processing the received classification data with a trained machine-based learning classifier.

The computer implemented simulator may be configured to simulate diamonds or diamondiferous objects and barren objects.

The computer implemented simulator may be configured to simulate photon emissions from the simulated objects as a result of simulated positron annihilation due to simulated irradiation of the simulated objects with photons of a predetermined energy at which giant dipole resonance (GDR) occurs due to nuclear reactions between the photons and carbon, wherein the computer simulated classification data is associated with simulated photons emitted from the simulated objects.

The computer implemented simulator may be configured to simulate a detector arrangement configured to detect the simulated photon emissions, wherein the computer simulated classification data comprises simulated output data from the simulated detector arrangement.

The computer implemented simulator may be configured to simulate travelling of simulated objects in a simulated object stream.

The computer implemented simulator may be configured to simulate attenuation and scattering of photons emitted from the simulated objects.

The method may comprise prior steps of:
receiving experimental classification data from diamond or diamondiferous test objects and barren test objects;
receiving physical property data corresponding to one or both of quantitative and qualitative aspects of the diamond or diamondiferous test objects and barren test objects; and
using one or both of the received experimental classification data and physical property data to validate the simulations generated by the computer implemented simulator by benchmarking the same to one or both of the received experimental and physical property data, wherein the method further comprises:
irradiating the diamond or diamondiferous test objects and barren test objects with photons of a predetermined energy at which giant dipole resonance (GDR) occurs due to a nuclear reaction between the photons and carbon; and
detecting photons of a predetermined energy level emitted from the irradiated objects by way of the detector arrangement and generating experimental classification data based on the detection of photons.

The method may comprise a prior step of training a machine-based learning classifier with computer simulated classification data generated by the computer implemented simulator to generate the trained machine-based learning classifier which is used to determine whether or not there is a strong likelihood that the object is potentially a diamond or diamondiferous.

The generation of the trained machined based learning classifier may comprise determining suitable architecture and weighting of the classifier. The computer simulated classification data may be generated by varying parameters of the computer implemented simulator and capturing at least computer simulated classification data corresponding thereto.

The data indicative of the varied parameters of the computer implemented parameters may be linked in a memory storage device with the corresponding resultant computer simulated classification data.

The method may comprise using at least part of the computer simulated classification data to validate the performance of the trained machine-based learning classifier.

The method may comprise storing weights and architecture of the trained machine-based learning classifier in a memory storage device.

The method may comprise classifying any potential diamond or diamondiferous object by way of the trained machine-based learning classifier; and storing information indicative of said classification in a memory storage device.

The method may comprise sorting objects based on the classification.

The machine-based learning classifier may in one example embodiment be in the form of a convolutional neural network.

The method may comprise:
irradiating the object with photons of a predetermined energy at which giant dipole resonance (GDR) occurs due to a nuclear reaction between the photons and carbon;
detecting back-to-back co-linear and co-incident gamma ray photons of a predetermined energy level emitted from the irradiated object by way of the detector arrangement, wherein the step of detecting is after a predetermined period of time after the step of irradiating.

The method may comprise detecting photons having an energy level of approximately 511 keV and rejecting photons not having the energy level of approximately 511 keV.

The classification data may be selected from a group comprising high and low data abstraction levels associated with output signals from the detector arrangement, and wherein the computer simulated classification data is matched to the classification data.

The lowest data abstraction level may be raw output signals from the detector arrangement and the highest data abstraction level may be a reconstructed 3D image based on one or more intervening data abstraction levels which effectively are based on the raw output signals.

The method may comprise receiving raw output signals from the detector arrangement and generating one or more higher data abstraction level data to be used as the classification data and computer simulated training data.

The method may comprise pre-processing the generated one or more higher data abstraction level data to improve the quality thereof prior to processing with the trained machine-based learning classifier.

The method may comprise generating a reconstructed a 3D image, based on lower data abstraction levels, which considers attenuation and scattering of photons emitted from the irradiated object.

The classification data may be reconstructed 3D images, the processing of the received classification data with the trained machine-based learning classifier comprises processing blocks of the 3D images in an overlapping fashion with the trained machine-based learning classifier.

The method may comprise detecting the presence of diamond in an object moving in an object stream within an object sorting system defining a path of travel of objects, wherein the method comprises separating from other objects those objects which are determined potentially to be diamond or diamondiferous in an on-line fashion.

The method may comprise detecting back-to-back co-linear and co-incident gamma ray photons with the detector arrangement along a line of response (LoR) which is transverse to the direction of travel of the object, wherein the classification data and computer simulated classification data comprises a plurality of lines of response.

The detector arrangement may comprise an array of detectors flanking a portion of the path of travel of the object, wherein the detectors have sensing axes substantially transverse to the direction of travel of the object.

The method may comprise generating a plurality of LoRs (Line of Response) which correspond to imaginary lines through the object connecting strikes on the detector array on opposite sides of the object, wherein the strikes correspond to the back-to-back co-linear and co-incident gamma ray photons emitted by the object as detected by the detector arrangement as raw output signals.

The method may comprise:
receiving a time-stamp of the strikes on the detector array on opposite sides of the path of travel of the object;
receiving or determining a speed of travel of the object;
using the time-stamp and the received/determined speed of travel of the object to shift the associated LoR to a stationary reference frame; and
maintain a record associating the LoR with information indicative of the specific associated object.

The method may comprise using generated LoRs to generate one or more of sinograms, 2D data and, 3D data.

The method may comprise transporting a plurality of objects on a conveyor belt in an object stream, and wherein the detector arrangement is located proximate to the conveyor belt.

According to a second aspect of the invention, there is provided a system for detecting presence of diamond in an object, the system comprising:
memory storage device; and
one or more processors configured to:
receive classification data associated with photons emitted from object as a result of positron annihilation due to irradiation of the object with photons of a predetermined energy at which giant dipole resonance (GDR) occurs due to a nuclear reaction between the photons and carbon, wherein the photons emitted are detected by a suitable detector arrangement; and
determine whether or not the object is potentially a diamond or diamondiferous by processing the received classification data with a trained machine-based learning classifier.

The one or more processors may be configured to implement the computer implemented simulator, wherein the computer implemented simulator is configured to simulate diamonds or diamondiferous objects and barren objects.

The computer implemented simulator may be configured to simulate photon emissions from the simulated objects as a result of simulated positron annihilation due to simulated irradiation of the simulated objects with photons of a predetermined energy at which giant dipole resonance (GDR) occurs due to nuclear reactions between the photons and carbon, wherein the computer simulated classification data is associated with simulated photons emitted from the simulated objects.

The computer implemented simulator may be configured to simulate a detector arrangement which detects the simulated photon emissions, wherein the computer simulated classification data comprises simulated output data from the simulated detector arrangement.

The system comprises a sorter configured to sort objects which are diamonds or diamondiferous from those that are barren.

A suitable architecture and weighting of the trained machine-based learning classifier may be stored in the memory storage device.

The computer implemented simulator may be configured to generate the computer simulated classification data by varying parameters of the computer implemented simulator and capturing computer simulated classification data corresponding thereto.

The data indicative of the varied parameters of the computer implemented parameters may be linked in a memory storage device with the corresponding resultant computer simulated classification data.

The one or more processors may be configured to classify any potential diamond or diamondiferous object by way of the trained machine-based learning classifier; and store information indicative of said classification in the memory storage device.

The one or more processor may be configured to identify a specific location of a diamond in the object by way of the trained machine-based learning classifier.

The machine-based learning classifier may be in the form of a convolutional neural network.

In some example embodiments, the system may comprise the detector arrangement.

The system may comprise a conveyor system comprising a conveyor belt configured to transport irradiated objects within the system.

The detector arrangement may comprise a pair of detector arrays oriented parallel to each other and having sensing axes transverse to the direction of travel of the belt.

The system may comprises an irradiator configured to irradiate the object with photons of a predetermined energy at which giant dipole resonance (GDR) occurs due to a nuclear reaction between the photons and carbon, wherein the detector arrangement is configured to detecting back-to-back co-linear and co-incident gamma ray photons of a predetermined energy level emitted from the irradiated object by way of the detector arrangement.

The detector arrangement may be configured to detect photons having an energy level of approximately 511 keV and reject photons not having the energy level of approximately 511 keV.

The classification data my be selected from a group of high and low data abstraction levels associated with output signals from the detector arrangement, wherein the computer simulated classification data is matched to the classification data.

The lowest data abstraction level may be raw output signals from the detector arrangement and the highest data abstraction level is a reconstructed 3D image based on one or more intervening data abstraction levels which effectively are based on the raw output signals.

The one or more processors may be configured to receive raw output signals from the detector arrangement and generate one or more higher data abstraction level data to be used as the classification data.

The one or more processors may be configured to pre-process the generated one or more higher data abstraction level data to improve the quality thereof prior to processing with the trained machine-based learning classifier.

The at least one processor may be configured to generate a reconstructed a 3D image, based on lower data abstraction levels, which considers attenuation and scattering of photons emitted from the irradiated object.

The classification data may be reconstructed 3D images, wherein the one or more processors is configured to process the received classification data with the trained machine-based learning classifier comprises processing blocks of the 3D images in an overlapping fashion with the trained machine-based learning classifier.

The detector arrangement may be configured to detect back-to-back co-linear and co-incident gamma ray photons along a line of response (LoR) which is transverse to the direction of travel of the object, wherein the classification data and computer simulated classification data comprises a plurality of lines of response.

The detector arrangement is configured to generate a plurality of LoRs which correspond to imaginary lines through the object connecting strikes on the detector array on opposite sides of the object, wherein the strikes correspond to the back-to-back co-linear and co-incident gamma ray photons emitted by the object as detected by the detector arrangement as raw output signals.

The one or more processors may be configured to:
  receive a time-stamp of the strikes on the detector array on opposite sides of the path of travel of the object;
  receive or determining a speed of travel of the object;
  using the time-stamp and the received/determined speed of travel of the object to shift the associated LoR to a stationary reference frame; and
  maintain a record in the memory storage device associating the LoR with information indicative of the specific associated object.

According to a third aspect of the invention, there is provided a computer-readable medium storing computer executable instructions which when executed on one or more processors cause said processors to:
  receive classification data associated with photons emitted from object as a result of positron annihilation due to irradiation of the object with photons of a predetermined energy at which giant dipole resonance (GDR) occurs due to a nuclear reaction between the photons and carbon, wherein the photons emitted are detected by a suitable detector arrangement; and
  determine whether or not the object is potentially a diamond or diamondiferous by processing the received classification data with a trained machine-based learning classifier.

In preferred example embodiments, the trained machine-based learning classifier is trained at least with computer simulated classification data from a computer implemented simulator which simulates s at least diamonds or diamondiferous objects.

It will be appreciated by those of reasonable skill in the art that the computer implemented medium may store computer executable instructions which when executed on one or more processors cause said processors to perform any method as described in the present specification.

According to a fourth aspect of the invention, there is provided a method for auditing output from a diamond mine, wherein the method comprises:
  detecting, at a diamond mine, presence of diamond in an object according to the method as described above;
  storing data associated with objects determined to be potentially a diamond or diamondiferous; and
  comparing the stored data with yield data from the diamond mine indicative of the yield of diamonds from the diamond mine.

It will be appreciated by those of reasonable skill in the art that at least some of the method steps described above with reference to the first aspect of the invention applies mutatis mutandis to the fourth aspect of the invention and will not be repeated herein for the sake of brevity.

According to a fifth aspect of the invention, there is provided a system for auditing output from a diamond mine, wherein the system comprises:

a memory storage device; and
one or more processors configured to:
    detect presence of diamond in an object using the system as describe according to the method as described above;
    storing data associated with objects determined to be potentially a diamond or diamondiferous; and
    comparing the stored data with yield data from the diamond mine indicative of the yield of diamonds from the diamond mine.

It will be appreciated by those of reasonable skill in the art that at least some of the method steps described above with reference to the first aspect of the invention applies mutatis mutandis to the fourth aspect of the invention and will not be repeated herein for the sake of brevity.

According to a sixth aspect of the invention, there is provided a method of training a machine-based learning classifier with computer simulated classification data generated by the computer implemented simulator to generate the trained machine-based learning classifier which is used to determine whether or not there is a strong likelihood that the object is potentially a diamond or diamondiferous.

It will be appreciated by those of reasonable skill in the art that at least some of the method steps described above with reference to the first aspect of the invention may apply mutatis mutandis to the sixth aspect of the invention and will not be repeated herein for the sake of brevity.

According to a seventh aspect of the invention, there is provided a system for training a machine-based learning classifier, wherein the system comprises:

a memory storage device; and
one or more processors configured to:
    train a machine-based learning classifier with computer simulated classification data generated by the computer implemented simulator to generate the trained machine-based learning classifier which is used to determine whether or not there is a strong likelihood that the object is potentially a diamond or diamondiferous.

It will be appreciated by those of reasonable skill in the art that at least some of the method steps described above with reference to the second aspect of the invention applies mutatis mutandis to the seventh aspect of the invention and will not be repeated herein for the sake of brevity.

DETAILED DESCRIPTION OF THE DRAWINGS

The following description of the invention is provided as an enabling teaching of the invention. Those skilled in the relevant art will recognise that many changes can be made to the embodiment described, while still attaining the beneficial results of the present invention. It will also be apparent that some of the desired benefits of the present invention can be attained by selecting some of the features of the present invention without utilising other features. Accordingly, those skilled in the art will recognise that modifications and adaptations to the present invention are possible, and may even be desirable in certain circumstances, and are a part of the present invention. Thus, the following description is provided as illustrative of the principles of the present invention and not a limitation thereof.

It will be appreciated that the phrase "for example," "such as", and variants thereof describe non-limiting embodiments of the presently disclosed subject matter. Reference in the specification to "one example embodiment", "another example embodiment", "some example embodiment", or variants thereof means that a particular feature, structure or characteristic described in connection with the embodiment(s) is included in at least one embodiment of the presently disclosed subject matter. Thus, the use of the phrase "one example embodiment", "another example embodiment", "some example embodiment", or variants thereof does not necessarily refer to the same embodiment(s).

Unless otherwise stated, some features of the subject matter described herein, which are, described in the context of separate embodiments for purposes of clarity, may also be provided in combination in a single embodiment. Similarly, various features of the subject matter disclosed herein which are described in the context of a single embodiment may also be provided separately or in any suitable sub-combination.

Figure 1:
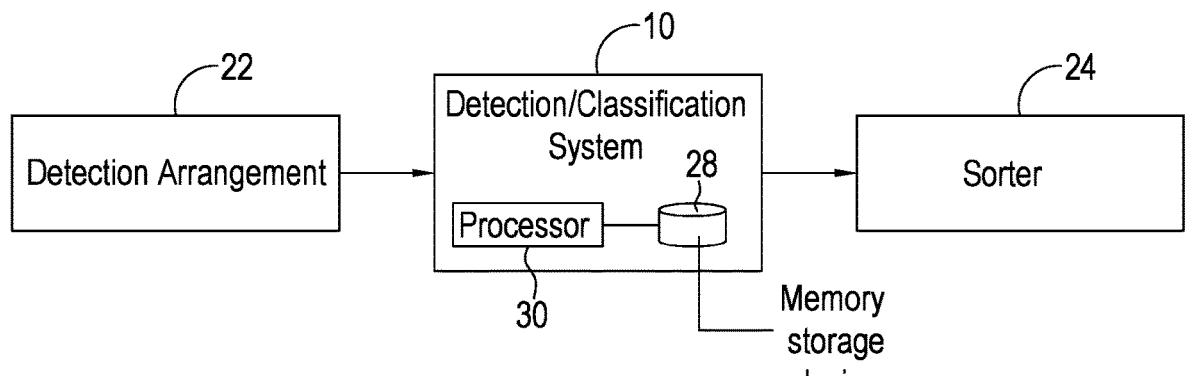
FIG. 1 shows a high-level block diagram of a system in accordance with an example embodiment of the invention.
Figure 2:
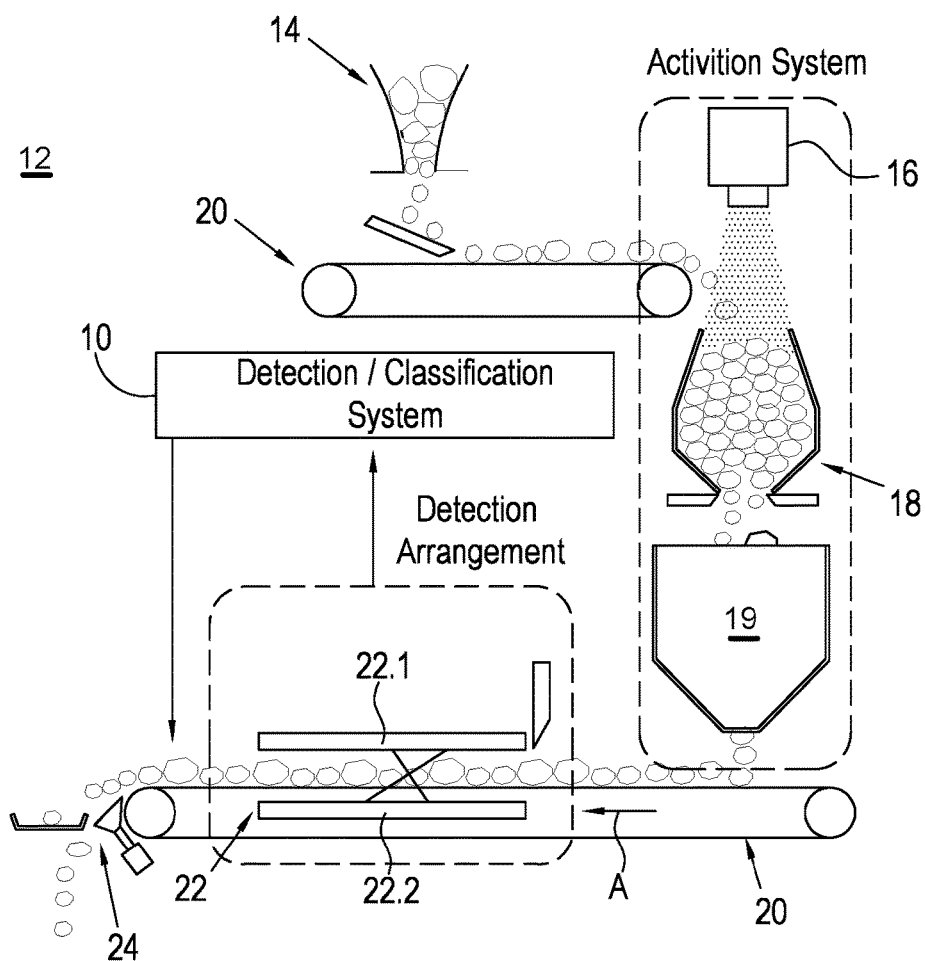
FIG. 2 shows a schematic diagram of mine processing system in accordance with an example embodiment of the invention including the system of FIG. 1.

Referring to FIGS. 1 and 2 of the drawings, a system in accordance with an example embodiment of the invention is generally indicated by reference numeral 10. The system 10 is typically a computer system configured to detect diamonds as individual, separate objects, as embedded in host objects or as objects included in a mass of other objects and as such is typically provided as part of a diamond mine processing system 12 as illustrated in FIG. 2.

The term "object" described herein may be understood to mean a rock particle such as kimberlite irrespective of the size thereof or a loose diamond. Thus the term object may be used interchangeably with the term rock or kimberlite or loose diamond herein.

The diamond mine processing system 12 may be located at or adjacent a diamond mine and may comprise suitable conventional mining equipment such as a crusher 14 to coarsely crush mined rock to sizes of approximately 160 mm diameter, or less. The system 12 further comprises a suitable irradiator 16 to irradiate the crushed rock with photons. The photons which irradiate the rock may be from gamma ray beams from bremsstrahlung of approximately 40 MeV electrons. Instead, or in addition, these photons may be from inverse Compton scattering, plasma wakefield device, or the like and thus it will be appreciated that the invention is therefore not limited to the specific exampled mentioned herein. In any event, the photons are at an energy at which giant dipole resonance (GDR) occurs due to a nuclear reaction between the photons and carbon in the rock.

The system 12 comprises a hopper 18 to hold the irradiated rock for a predetermined period of time. The irradiated rock returns to moderate levels of specific activity within minutes, by which time PET isotopes represent the dominant residual activity. In this regard, the hopper 19 is configured to hold the irradiated rock for a hold-time of between twenty and thirty minutes at which time the $^{11}$C pet isotope is the dominant activity. The hopper 19 may then automatically release the rock after the hold-time.

The system 12 conveniently comprises conveyor arrangement 20 comprising suitable conveyor belts which are non-attenuating to PET photons to transport rock in the system 12 in an automated fashion. The conveyor arrangement 20 may be configured to transport rock in a rock stream at a constant predetermined speed in the system 12, for example, 1 m per second.

The system also comprises a detector arrangement 22 which is located downstream from the hopper 18 and adjacent the conveyor arrangement 20, particularly the belt thereof, so as to detect PET photons emitted therefrom. In one example embodiment, the detector arrangement 22 comprises a pair of detector arrays 22.1 and 22.2 which are located above and below the belt so as to be seen to effectively sandwich the belt and rock travelling thereon. The arrays 22.1, 22.2 have sensing axes which are substantially transverse to a direction of travel A of the rock. In one example embodiment, the detector arrangement 22 comprises detectors suitable for detecting photons. In this regard the detectors of the arrangement 22 may be in the form of scintillator crystals and photomultiplier tube (PMT) detectors with suitable electronics.

The system 12 also comprises a suitable sorter 24 which may be an electronically controlled mechanical sorter 24 configured to sort potentially diamondiferous or in other words diamond containing rocks or loose diamonds from potentially barren rocks or in other words rocks without diamonds therein.

The system 10 as described herein is communicatively coupled to the detector arrangement 22 and to the sorter 24 so as to receive classification data from the detector arrangement 22 and to generate suitable control signals to control the sorter 24 to sort diamondiferous rocks from barren rocks. In this regard, one aspect of the present invention is to process the classification data with sufficient speed in order to be able to send the activation signal (data) to the sorter 24 in time.

The sorter 24 may be configured to sort diamonds or diamondiferous rocks into one or more categories according to one or more specific properties of the diamond/diamondiferous rock detected, as opposed to simply sorting the same from barren rocks.

The system 10 may be coupled to the arrangement 22 and/or the sorter 24 in a hardwired fashion, or in a wireless fashion. In one example embodiment, the system is communicatively coupled to the arrangement 22 via a communications network which may comprise one or more different types of communication networks. In this regard, the communication network may be one or more of the Internet, a local area network (LAN), a wide area network (WAN), a metropolitan area network (MAN), various types of telephone networks (e.g., Public Switch Telephone Networks (PSTN) with Digital Subscriber Line (DSL) technology) or mobile networks (e.g., Global System Mobile (GSM) communication, General Packet Radio Service (GPRS), Code Division Multiple Access (CDMA), and other suitable mobile telecommunication network technologies), or any combination thereof. It therefore follows that though it may not necessarily be practical, it is envisaged that in some example embodiments, the system 10 need not be at the site of the mine but may be remote therefrom.

The system 10 may comprise a memory storage device 28 and a processor 30 configured to perform various data processing and control operations to detect potentially diamondiferous material as described herein.

The processor 30 may be one or more processors in the form of programmable processors executing one or more computer programs to perform actions by operating on input data and generating outputs. The processor 30 as well as any computing device referred to herein, may be any kind of electronic device with data processing capabilities including, by way of non-limiting example, a general processor, a graphics processing unit (GPU), a digital signal processor (DSP), a microcontroller, a field programmable gate array (FPGA), an application specific integrated circuit (ASIC), or any other electronic computing device comprising one or more processors of any kind, or any combination thereof. For brevity, steps described as being performed by the system 10 may be steps which are effectively performed by the processor 30 and vice versa unless otherwise indicated.

The memory storage device 28 may be in the form of computer-readable medium including system memory and including random access memory (RAM) devices, cache memories, non-volatile or back-up memories such as programmable or flash memories, read-only memories (ROM), etc. In addition, the device 28 may be considered to include memory storage physically located elsewhere in the system 10, e.g. any cache memory in the processor 30 as well as any storage capacity used as a virtual memory, e.g., as stored on a mass storage device.

Though not illustrated, it will be appreciated that the system 10 may comprise one or more user input devices (e.g., a keyboard, a mouse, imaging device, scanner, microphone) and one or more output devices (e.g., a Liquid Crystal Display (LCD) panel, a sound playback device (speaker), switches, valve, etc.).

The computer programs executable by the processor 30 may be written in any form of programming language, including compiled or interpreted languages, declarative or procedural languages, and can be deployed in any form, including as a stand-alone program or as a module, component, subroutine, object, or other unit suitable for use in a computing environment. The computer program may, but need not, correspond to a file in a file system. The program can be stored in a portion of a file that holds other programs or data (e.g., one or more scripts stored in a mark-up language document), in a single file dedicated to the program in question, or in multiple coordinated files (e.g., files that store one or more modules, sub-programs, or portions of code). The computer program can be deployed to be executed by one processor or by multiple processors 30, even those distributed across multiple locations.

The computer programs may be stored in the memory store 28 or in memory provided in the processor 30. Though not illustrated or discussed herein, it will be appreciated by those skilled in the field of invention that the system 10 may comprise a plurality of logic components, electronics, driver circuits, peripheral devices, etc. not described herein for brevity.

The processor 30 is configured/programmed to receive classification data from a classification data source in one or more data abstraction levels as will be described below. Moreover, and more importantly, the processor 30 is configured to determine whether or not the object is potentially a diamond or diamondiferous by processing the received classification data with a trained machine-based learning classifier (hereinafter referred to the "classifier") as will be described in more detail below.

Figure 3:
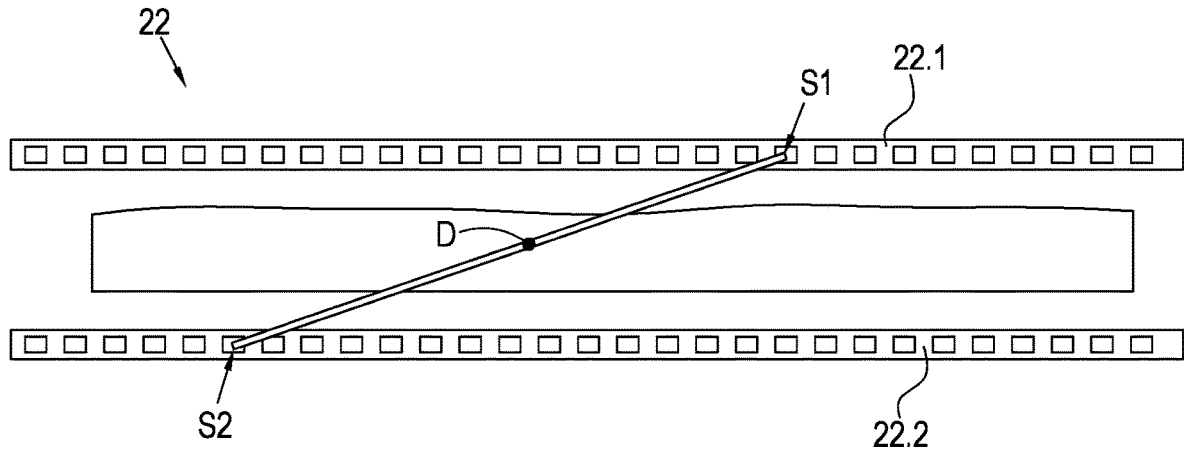
FIG. 3 shows an illustration of Kimberlite rock on a moving belt between detectors arrays in accordance with an example embodiment of the invention, showing a 2 coincident back-to-back 511 keV gamma rays, which together form a Line of Response (LoR)

The classification data received by the processor 30 is typically associated with photons detected by the arrangement 22 which are emitted from object as a result of positron annihilation in the irradiated object received from the hopper 18. In particular, referring to FIG. 3 of the drawings when a PET isotope in the kimberlite rock releases a positron particle through beta-decay, the positron annihilates with a nearby electron after following a short path that can involve multiple scattering events. The most common outcome of this annihilation is the production of nearly co-linear back-to-back 511 keV gamma ray photons. Each photon then travels through the surrounding material, sometimes changing energy and direction along the way. When the photons reaches the detector arrangement arrays 22.1, 22.2 at S1, S2, the arrangement 22 outputs classification data in the form of detector strike/hit event data, for example, which comprises data indicative of the location of the hit on the array 22.1, 22.2, the energy of the photon, and a time stamp. Millions of these hit events can result for a given rock scan.

Figure 4:
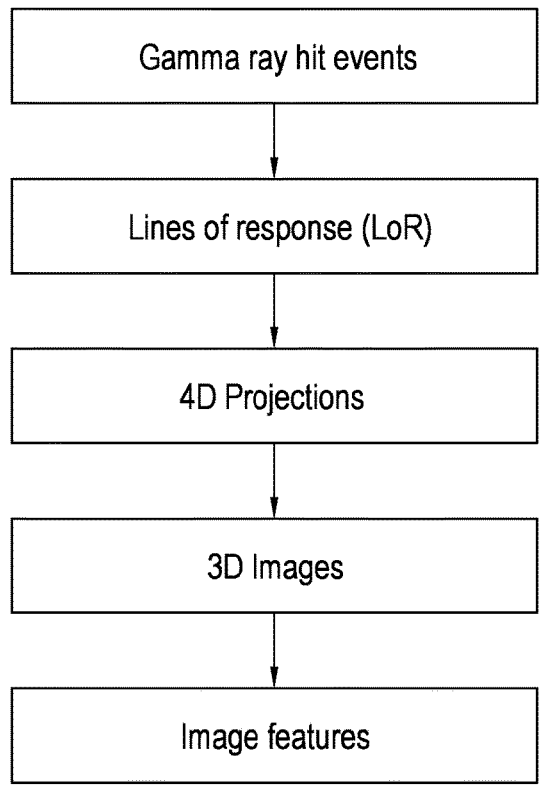
FIG. 4 shows block diagram of the various levels of the abstraction of the classification data in accordance with an example embodiment of the invention.

As mentioned above, and with reference to FIG. 4 of the drawings, the term "classification data" as described herein may be considered to include any data associated with outputs from the detector arrangement 22 in response to photons of the type described above being incident thereon/detected thereby. It follows that the classification data may have different levels of data abstraction each being associated with the photons detected by the arrangement 12 as increasing in level of abstraction from gamma ray strikes/hit event data on the detector arrangement 22, lines of response (LoR), 4D projections, 3D images, and to image features extracted from the images as will be discussed below. It will be understood that the 4D projections are essentially 4D data, being 2D sets of 2D projections.

As described above, the processor 30 may be configured to receive any type classification data described herein from the detector source including: classification data in the form of raw signal data from the arrangement 22 in which the arrangement 22 is the classification data source, and higher-level data abstraction level classification data from one or more pre-processing system/s and/or computing devices. To this end, though the processor 30 is illustrated in FIGS. 1 and 2 to be coupled directly to the detector arrangement 22, nothing precludes the processor 30 from simply receiving the outputs of the detector arrangement 22 indicative of detected photons in any level of data abstraction from a suitable classification data source in the form of the pre-processing system/s and/or computing devices, or the like.

Instead, or in addition, the processor 30 may be configured to receive, and process, classification data in the form of raw signal data from the arrangement 22, as well as data from any other abstraction level, to any desired data abstraction level as will be understood by those skilled in the invention. In this regard, the description which follows pertaining to the classification data of various data abstraction levels need not be limited to interpretation as being done by the processor 30 as the processor 30 may generate the classification data in the fashion described below or may simply receive the detection data as input data thereto from a suitable data source as the case may be.

Referring again to FIG. 4, in case where classification data is in the form of lines of response (LoR), hit events/strikes on the detector arrays 22.1, 22.2 are paired with the time stamp thereof (within a tolerance) to define a line of response (LoR) which is the line that connects the two hit locations S1 and S2. LoR data consists of the positions of the two end points, the photon energies and the timestamp for each LoR.

Since the rock is moving on a belt, gamma ray hits occur along the length of the detector arrays 22.1, 22.2 which may be over a metre long. To image a certain section (region of interest) of moving rocks, the LoRs in that section have to be shifted to a central stationary reference frame based on the belt velocity and the time stamp. This isolated region of shifted LoR data is then a virtual basket of rocks processed for image reconstruction and diamond detection as will be described below.

In one example embodiment, the belt of rocks is typically divided into a moving slightly overlapping train of sections (regions of interest—RoIs) where each one is initiated at a point where the belt enters the detector arrangement 22 and is tracked until a decision about a possible diamond is reached just before the sorter 24. Imaging and diamond detection must occur during this tracking period so that diamond bearing rocks are timeously isolated from the belt via the sorter 24. Beyond the sorter 24, the moving section ceases to be of interest. In one example embodiment, there is provided a separate processor 30 for each moving section to perform the imaging/detection and tracking for that section. After the section has been tracked to the sorter 24 a newly initiated region of interest near the beginning of the detector arrangement 22 is assigned to the processor 30.

Figure 5:
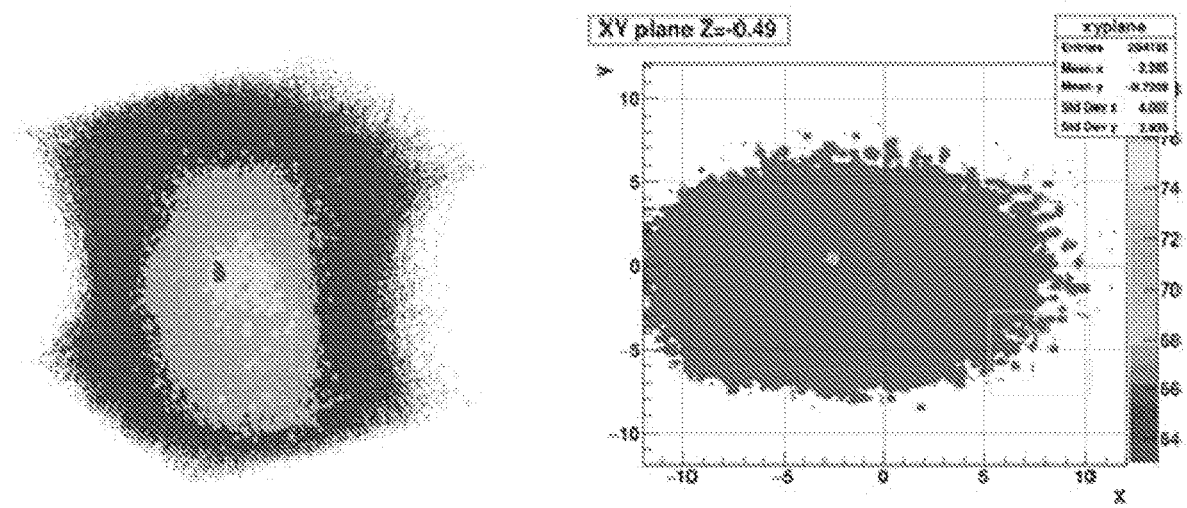
FIG. 5 shows an unfiltered back projection for a larger diamond (10 mm size) in a 100 mm rock in accordance with an example embodiment of the invention, wherein the first image on the left is the 3D voxel space representation, and the next image on the right is a slice through this space at the level of the diamond.

In the case where classification data is in the form of many 2D projections from a 4D sets as described above, after the LoRs have been shifted into a stationary reference frame (to remove the effect of belt motion) as described above, they are grouped into families with the same spatial direction (a given set of two spherical coordinate angles $(\theta, \varphi)$). For each family, the LoR intersections with a 2D plane located midway between the detector arrays 22.1, 22.2 form a 2D projection. All 2D projections of the type described make up a single 4D sinogram. The plurality of LoRs may be used to create a back-projection as illustrated in FIG. 5, which shows a 100 mm kimberlite rock back-projection with a 10 mm diamond therein.

It will be appreciated that the unfiltered back-projection may not the best form of classification data to use as it suffers from a distortion where each voxel is effectively convoluted with an approximately inverse square function of distance. It is therefore preferable to reconstruct the original source point density distribution. To this end, in the case where the classification data is in the form of 3D images, iterative 3D tomography is employed which makes use of a Maximum Likelihood Estimation Method (MLEM) algorithm, or any other iterative reconstruction algorithm, to reconstruct an image of the source point density distribution using the set of 2D projections (sinogram).

Figure 6:
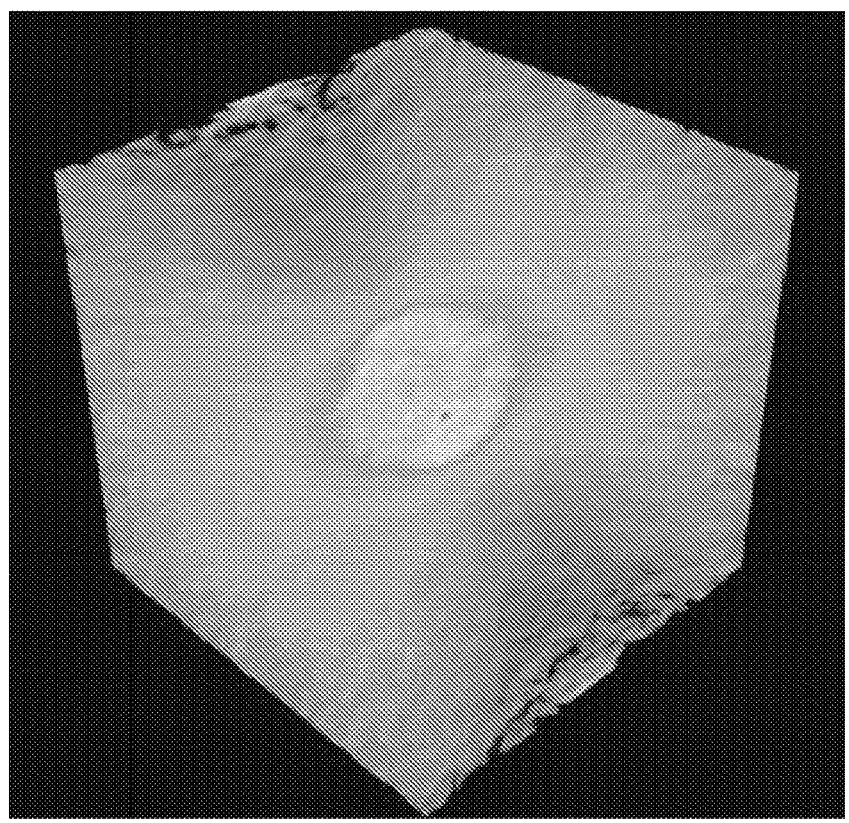
FIG. 6 shows a reconstructed image for a single 100 mm rock containing a 7 mm diamond.

Referring to FIG. 6, a reconstructed image for a single 100 mm rock containing a 7 mm diamond is shown.

The 3D image created from the processing of the sinogram described herein to a PET reconstructed image should ideally reflect the original PET isotope source point density distribution. Two effects are very important to treat in this respect. These are the attenuation and scattering of the two back-to-back co-linear and co-incident 511 keV photons as they travel through the kimberlite medium. This effect means that typically only 3% of the photons are usable in the LoR construction process. The attenuated photons are lost and the scattered photons lead to a false LoR reconstruction. The size of the effect is dependent on the local geometry of the PET isotope. When on average the path length of LOR in the rock is long, then the effect is stronger. Gaps in the rock bed and the position of the PET isotope source point in the rock affect this path length. A PET image reconstruction method that does not take this effect into account will treat the increased manifestation of LoRs associated with open areas or edge areas as increased concentrations of PET source points. For example, a single spherical rock which had a uniform distribution of PET isotope source points would be reconstructed as having a radially increased distribution of PET isotope source points. An algorithm is used to treat the effects of attenuation and scattering in the PET image reconstruction, so that the systematic effects of attenuation and scattering do not lead to a mismatch between the actual distribution of PET isotope source points and the reconstructed one as described.

It will be understood that elementary unit of a PET image is the Line of Response (LoR), resulting position sensitive detection of a single positron annihilation event by the arrangement 22. In this regard, approximately a million such events are required per rock (10 cm diameter) in order to detect diamonds therein. The LoR must be processed into PET reconstructed images in 3D with voxel sizes of millimetric dimensions. It follows that hundreds of these images must be analysed per second in a typical 700 tph throughput. Thus the processor 30 implementing the classifier as described herein is if great importance to detect diamonds as the belt is moving as other techniques will fail in attempting to due so based on the computational burden of this on-line/site-of-mine determination.

The processor 30 is able not only to determine whether or not the rock has a possible diamond therein or not but also determine the size and location of a possible diamond in the rock. Moreover, the processor 30 is configured to determine whether or not there are liberated diamonds in stream of rocks. In this regard, in the present description, reference will be made to the processor 30 detecting diamonds (e.g., diamonds liberated from rocks during crushing) or diamondiferous objects, it follows that any explanation which follows which makes reference to detecting diamonds may be understood to also detect diamondiferous objects, and vice versa. In some example embodiments, the processor 30 may be configured, by way of the classifier, to classify a diamond detected in a rock in terms of shape and/or size.

In a preferred example embodiment, the processor 30 is implemented by a GPU which is size constrained. Therefore classification data in the form of 3D images to be processed by the classifier must therefore be segmented to a specific volumetric size matched to the computing system resources. The 3D images for the whole rock stream are therefore partitioned to be processed as 3D blocks by the classifier. Because the diamond represents a local increase of the PET isotope density, and because the there is an irreducible PET isotope background, and further, because the image statistics are local geometry dependent, it is necessary to ensure that a candidate diamond represented by a local PET isotope hotspot be completely surrounded in 3D by a region that should represent background.

To achieve the aforementioned, the blocks of 3D data which is processed by the classifier are arranged to always be overlapping, so that the search through the volume will always have a diamond which may be at the edge of one block sufficiently deep in another block.

In the case where the classification data is in the form of image features, it will be noted that image processing techniques are applied to images generated above. Each image reconstruction contains a large number of bright spots (blobs). For large diamonds >8 mm in diameter the brightest blob is the diamond. As the diamond size gets smaller it gets lost in the background. Many blob features must be evaluated to correctly classify blobs as diamonds or background. A blob finder algorithm is used to locate blob features in each image. For each blob the following is calculated:

Blob position in voxel units (x of voxel, y of voxel, z of voxel), This is used to calculate the range (radius from rock centres)

Blob eccentricity giving a metric on blob shape

Peak value (signal)

Integrated brightness after background subtraction (mass)

Image brightness is higher at the edges of rocks, because at the edges LoRs (depending on angle) can reach the detectors after passing through a shorter length of kimberlite, reducing the number of LoRs that are lost due to scattering or absorption. In one example embodiment, position input may help the classifier incorporate this fact, allowing attenuation and scattering to be accounted for in the machine learning. This attenuation and scattering also affects background noise which may hide diamond signals at the edges. For this reason, the blob significance is also calculated to incorporate this effect.

Figure 7:
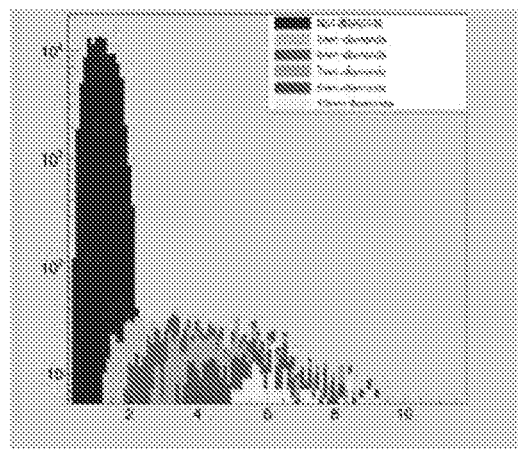
FIG. 7 shows a stacked significance log histogram of blobs for all rocks.

In one example embodiment which will be clearer in view of the description which follows below, the labelling of blobs as diamonds or not diamonds is done by matching blob positions to the known diamond position used in the kimberlite geometry input file for the Geant4 simulations. The resulting data set is imbalanced as there are significantly more non-diamond background blobs than diamond blobs. In FIG. 7, the distribution of image features for a range of diamond sizes is shown. The classifier is configured to exploit these trends in order to identify diamond containing rocks.

In this regard, it will be noted that the trained machine-based learning classifier implemented by the processor 30 as described herein is trained at least with computer simulated classification data from a computer implemented simulator which simulates diamonds or diamondiferous rocks as well as barren rocks. The classifier may conveniently be any artificial intelligence (AI) classifier. The term "classifier" may therefore be used interchangeably with "AI" herein.

The classifier may be selected from a group comprising a Decision Tree Classifier, Random Forest Classifier, Ada Boost Classifier, K-Nearest Neighbors Classifier, a Support vector machine, Quadratic Discriminant Analysis, Gaussian Process Classifier, a Multi-layer Perceptron Classifier, preferably a Convolutional Neural Network. Notwithstanding, it will be noted that other machine learning classifier may be used in the present invention.

As mentioned, the classifier as described herein is typically trained by way of simulated classification data from a suitable computer implemented simulator. The processor 30 may be configured to implement the computer simulator as described herein. To this end, it will be noted that classification data is required to train the classifier to use received classification data to detect a potentially diamondiferous rock. However, classification data is acquired by positron emission tomography in the manner as described above and for the purposes of training the classifier in accordance with the invention, a problem exists in that it is not practically feasible to acquire a large amounts of classification data experimentally for this training especially where there is prior knowledge of the truth of whether or not an object is diamondiferous.

Moreover, the training classification data for the classifier needs to be representative of a large variety of cases where the properties of the object to be sorted are to be varied in a parameter space relevant to the diamondiferous and barren objects. Examples of these properties or physical parameters are geometric size and shape and relative quantities of various materials in the composition of the object, and the like.

The parameters describing the detector arrangement also need to be varied. These could be quantities relating to detection limits, interrogating power, configuration of the sensors in terms of thresholds, array types and geometries, electronic processing capacities, sensitivities to various materials or emanations from these materials, and the like.

The statistical quantity of information gathered is another parameter, relating to the power of the system and/or the throughput rate. The training data therefore typically contains a very large number of elements. It is therefore generally not efficient to manually create a data set.

Hence, the processor 30 is conveniently configured to implement the simulator as described herein wherein the simulator is based on very precise modelling of the sensor-based sorting process, from its initial detection, right through to the generation of the classification data to be presented to the classifier for processing. The modelling uses a sufficiently accurate physics and engineering description of this process. This simulator is then benchmarked with experimental data.

In one example embodiment, generation and/or implementation of the simulator may be achieved by way of at least software to model subatomic particle processes and various particle detector geometries known as Geant4 (referred to briefly above) which is used by various research groups including those at the Large Hadron Collider at the European Organization for Nuclear Research (CERN). This is a C++ toolkit used by researchers to simulate particle histories and the behaviour of the detector arrays used to study these histories.

The computer simulation performance in accuracy to the real situation is very carefully benchmarked in experiments under very similar conditions. The advantage is that much fewer experiments need to be performed compared to a full experimental production of the training data.

It will be appreciated that the processes described herein with respect to the simulator as all computer simulated processes.

In one example embodiment, the simulator is based on the Monte Carlo technique benchmarked to a small experimental data set. As mentioned, the full physics of PET from the initial activation of the PET activity in the material by a photon beam at the energy of the Giant Dipole Resonance (GDR), to the registration of the primary signal in the detector arrangement 22 is used, in of course the simulation. The detector hits lead to the construction of Lines of Response (LoR). A back projection may be assembled as a 3D image from the LoRs. The LoRs may also be binned into a 4D sinogram, as a set of transverse (x,y) projections for a set $(\theta, \varphi)$ of angles. The sinogram can be converted to a PET reconstruction as a quantitative 3D image of source points by a variety of techniques known in the art as described herein which finds the most likely original 3D source point density.

With simulations generated by the simulator, one knows the truth, which means, one knows the full details of whether a diamond was inserted or not into the kimberlite, and all the parameters describing the diamond and the kimberlite, as well as the detection system 10 performance. Thus the computer simulated classification data generated by the simulator may be segmented into a training and a validation dataset as will be described below. In principle, the simulated classification dataset can be large, as high-performance computing techniques can be used to generate it offline to the run-of-mine detection scenario. The dataset can be validated by selected experiments to benchmark the computer simulation at a variety of points that explore the full parameter space of the diamond-kimberlite-detector system. The point is that much fewer experiments are necessary than if the full training and validation data set was done by experiment alone.

The simulator may be referred to as a simulation or computer model, whatever the nomenclature, simulator virtually simulates the detector array 22.1, 22.2, and positron events in mined kimberlite rock to provide LoR data.

It will be noted that the simulator incorporates all run-of-mine operating conditions, comprising on or more simulations of:

Correct detector geometry and materials, down to the detector scintillating pixel level of detail.

Realistic model of kimberlite rock (physical property data including size and shape distributions and material composition).

Realistic model of the activation system including the primary electron beam with full details of the scanning and fanning system. The bremsstrahlung photon production target, the evolving mixed radiation field, the electromagnetic and nuclear physics for the beam kimberlite interaction, detailing the production of all residue nuclides and once again the secondary projectiles which may also interact further. This leads to the correct PET isotope source activity with modelling of all singles and coincident backgrounds.

The inventory of carbon activity and also other positron emitting background isotopes are used to generate the positrons which ultimately produce the LoR candidates. Positrons annihilate and photons are tracked to the detector pixels respecting the full physics including the effects of attenuation and scattering.

Realistic detector response simulating realistic gamma ray hit detection and behaviour of the electronics (sensitive detector hits and digitisation)

Correct belt operation, so the simulation moves the belt in time slices at a constant velocity Correct hopper 18 holding times are modelled, allowing for different lifetimes of different activated PET and non-PET isotopes.

Realistic LoR creation exactly as in a real experiment. In fact the input to the data processing chain, leading to the AI processing, can be either real experimental data or simulated data, as both output the same data structures.

For various set diamond sizes, or a continuous range of sizes, many single simulated rocks were seeded with a single diamond at a random location within the rock as run through a simulated mining system in order to create training data for the classifier described herein. The simulator is benchmarked against experiments in various scenarios. An iterative process of development of experiment sophistication and simulation detail and accuracy was followed to convergence between the simulation and the experiment.

This is an important aspect of the invention described herein as it is important to have very large data set where the truth is known, which can be divided into a training and a validation data set.

In some example embodiments, the simulator is used to fine tune and optimise parameters for the image reconstruction and classification by the classifier by optimising:

the energy threshold for the 511 keV gamma photon detection to be used to keep or reject LOR data as it pertains to image quality and classifier classification. This allows us to set the rejection of Compton Scattered events, thereby cleaning the LOR data set of the systematic effect of photon scattering.

The classifier may recognise that the scattering occurred in the kimberlite or the detector. This uses the multi-hit capacity of the detector, with reconstruction of in-detector Compton events the methods to create PET projections by investigating various ways to define solid angle LOR families as these pertain to image quality and improved classifier classification. This relates to non-uniform binning strategies for LORs based on considerations of image statistics, planar coverage, optimisation of resolution in angle phase space, position phase space and ultimately in the reconstruction 3D voxel space and considerations of the speed of reconstruction.

the methods to partially populate surrounding projection pixels to a LOR intersection with the projection plane, including but not limited to Gaussian methods, as these pertain to image quality and improved classifier classification. This aspect relates to a representation of a LOR within a discretised environment while accommodating statistical considerations related to the system point spread function and other performance metrics.

the pre-processing of reconstructed images, including but not limited to normalization and contrast correction, as this pertains to improved diamond classification the use of multiple AI stages to correctly classify a large range of diamond sizes where each stage is trained on a smaller size range that overlaps with the ranges of neighbouring stages. Each range of diamonds size to be discovered is seen as meriting its own method specialised to its discovery.

In summary, the computer simulated detection data is obtained by varying the aforementioned parameters of the simulator and obtaining suitable computer simulated classification data. The computer simulated classification data generated with varied parameters of the simulator provides the system 10 with a robust training, and validation dataset, which therefore optimises the performance of the classifier described herein which enables fast and less computationally exhaustive means to detect diamonds in rocks in a mining system.

It will be understood by those skilled in the art that the computer simulated classification data obtained from the simulator and described herein, as well the classification data received by the processor 30, in use, may correspond mutatis mutandis to any of the data abstraction levels contemplated herein.

In the presence of a diamond within kimberlite resides in the information content of the data. Its revelation in the data can be evidenced in a number of levels of data processing before processing by the classifier. Firstly and most primitively, a back-projection 3D image can be formed, or a PET reconstruction 3D image can be formed, and then metadata extracted for the blobs as a set of blob-parameters (significance of signal to background, blob signal strength, blob geometry, blob apparent position within the rock, etc). Secondly the LoR back-projection image is processed with the classifier. Thirdly, the classifier could process the PET reconstruction of the 3D source point density. Fourthly, the classifier may process the sinogram. As mentioned above, the 3D images are essentially processed versions of the raw data from the arrangement 22, where some information may still be lost, or where some systematic effects in the physics may not be accounted for. However, the 3D representations are more integrated, summarised or compact forms of the data which are more amenable to the training of the classifier. The sinogram is a more abstract visual entity which is the least processed entity, with the least modification but the most original information content. In terms of training the classifier, the complexity increases as the (data-summarising) processing of the data decreases and the quantity of data for a single rock increases. This would be in the order blob-metadata, back-projection image, PET reconstruction image and sinogram. This invention would pertain to the application selection, training, validation and configuration, of the machine learning algorithm to any of these data types which, from the foregoing, may all be considered classification data.

In any event, it will be understood that the computer simulated classification data from the simulator may be separated into training data/dataset and/validating data/dataset which used to train the classifier. It will be noted that the training may be to obtain the initial weightings and architecture of the classifier and the validation may be so as to confirm the accuracy of the training and/or re-configure/tune the architecture and/or weightings of the classifier.

The processor 30 is configured to determine in a binary yes/no fashion whether or not a rock from the moving conveyor belt needs to be sorted by the sorter 24 for further processing to recover hidden diamonds. Since diamonds are scarce in mined ore it is essential that the classifier maximises the number of true-positives and minimises the number of false-negatives (minimal false positives are acceptable). This is especially important as the training and testing data is imbalanced with more negative cases than positive ones. Evaluating each classifier on training and test data will ensure accuracy and generality. Recall and precision metrics are used to evaluate each classifier to be used for the diamond detection system. Recall measures the ability to correctly detect true positives and precision measures the ability not to detect false positives. For a good classifier these metrics must be as close to unity as possible.

Though many types of classifiers of the type described above may be used for the purposes of classifying the invention, the present invention preferably makes use of Multi-Layer Perceptron (MLP) classifier and particularly a Convolutional Neural Network (CNN) based classifier as the other classifiers have not achieved the same level of performance as the preferred classifiers during experimentation.

In one example embodiment, the MLP classifier with one hidden layer and approximately five perceptrons may be trained with classification data in the form of image features as described above to yield a classifier to detect diamonds of 7 mm and above.

In a preferred example embodiment, the classifier is a deep-learning network for image object identification in the form of a convolutional neural networks (CNN). The CNN classifier uses various convolution layers as well as other complex perceptron layers such as pooling layers to learn how to identify image features such as edges, bright spots, degree of image uniformity among others. In one example embodiment, the CNN classifier is used to identify diamonds within classification data in the form of reconstructed images.

Images of barren blocks are more uniform whereas the diamondiferous block contains a distinct feature. Image properties such as these (as well as unexpected, non-trivial ones) are learnt by the CNN classifier in order to perform accurate classifications.

Although the training of the CNN classifier can take a significant amount of time, once trained the CNN classifier can be easily saved on a memory associated with the processor 30 or the device 28 and recalled at a future date to speedily identify diamond-containing ROIs using unclassified block input.

It will be noted that the CNN classifier is preferable as it accepts low data abstraction inputs (images and possibly others such as LoR and projections) whereas others operate on very high data abstraction which may lose important classification data information present in the lower levels.

The CNN classifier self-discovers pattern matching and image features to use as opposed to other methods. In this way more sophisticated AI can discover representations of the original data at higher levels of abstraction. This can happen at depth, meaning it can do this representation discovery over several layers. These new representations are expected to extract essential features of the data which are sensitive to complex aspects of the decision making.

The CNN is advantageous in that once it is trained and the model (weights and architecture) saved to file, it may be recalled for use on experimental or more validation data. A classifier such as a K-nearest neighbours requires the entire training data set to be stored in RAM so that it can be used for classification which is impractical for run-of-mine circumstances.

The CNN classifier is more suited to go beyond simple binary yes/no diamond to include other classifications such as size, shape metrics for example to be used for auditing or calculating some sort of profit figure of merit perhaps or to guide selective rock sorting.

The CNN classifier is trained to analyse a region around the diamond, and not just the diamond itself. In this way, a trained CNN classifier is able to analyse the diamond signal in the context of its background. For example, a smaller signal in a smaller background region can be classified as a diamond, whereas the same size signal in a higher activity region might be just statistical noise. For the 3D image, the classifier recognises a potential diamond in 3D (whereas a human would do this on a 2D image), and in the LoR case, the classifier would do this in 4D. In this regard, the present invention enables detection of a diamond or diamondiferous material in a manner which is beyond a human inspection of the data.

The CNN classifier may be configured to learn aspects of the signal that are characteristic of diamonds independent of either their position in the image or their scale. For example, training the CNN classifier on a small diamond in the top left of an image can help it to identify a larger diamond in the bottom right. Moreover, the CNN classifier is able to take a low-statistics image reconstruction, predict the high-stats image and segment rocks to aid rock selection and ejection.

In one example embodiment, a CNN classifier is configured to internally learn about image attenuation and other photon effects to create more accurate images which are used for the classifications. The improved imaging would be within the CNN classifier so in terms of input and outputs: sensor data→initial imaging→CNN (doing internal attenuation/scattering correction to create internal high-quality images)→classification.

The lower limit of the CNN classifier detection of diamond size is limited by the image background noise and the quality of the PET reconstruction. In practice many CNN classifiers, each trained over separate overlapping diamond size ranges, can be used to find all required diamond sizes. Very large diamonds can also be detected by the easy to calculate 'quasi-image' back-projection which would show large bright hotspots which signify large diamonds.

Instead of using the highly abstract reconstructed image data, input data with lower abstraction can be used to train the CNNs from using raw LoR data to using only 4D sinograms.

Figure 8:
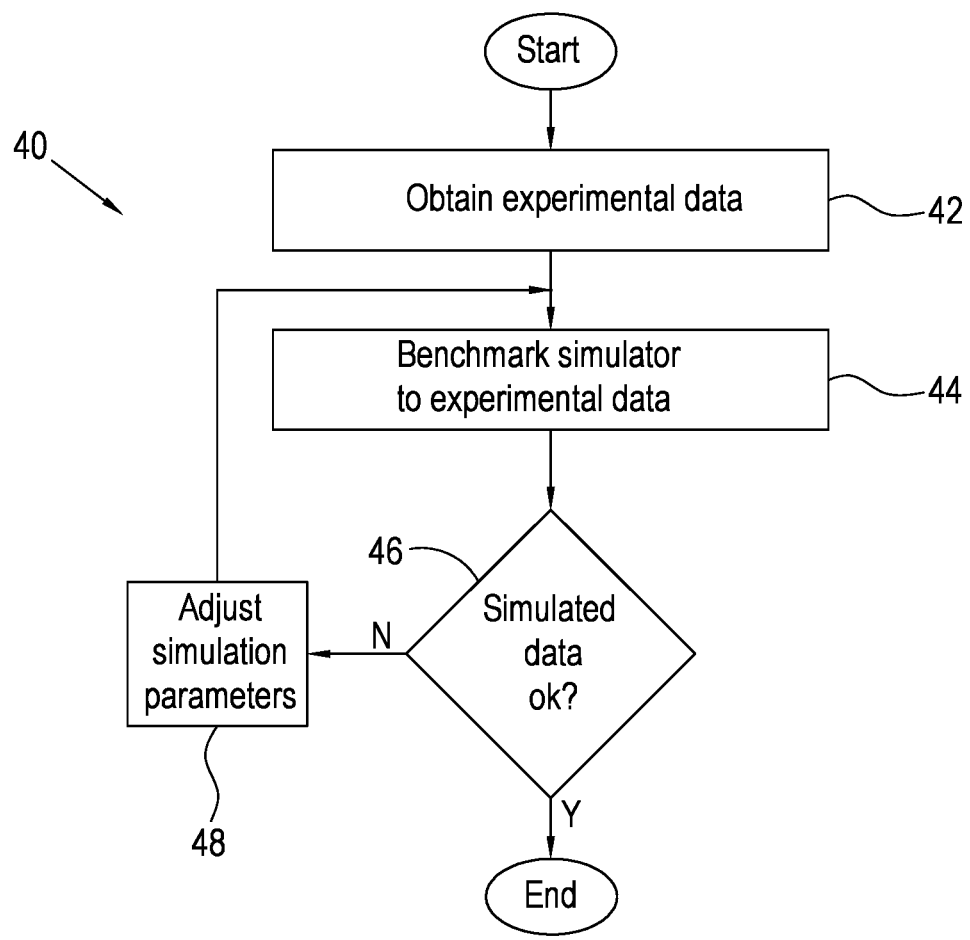
FIG. 8 shows a high-level flow diagram of a method for generating the computer implemented simulator in accordance with an example embodiment of the invention.
Figure 9:
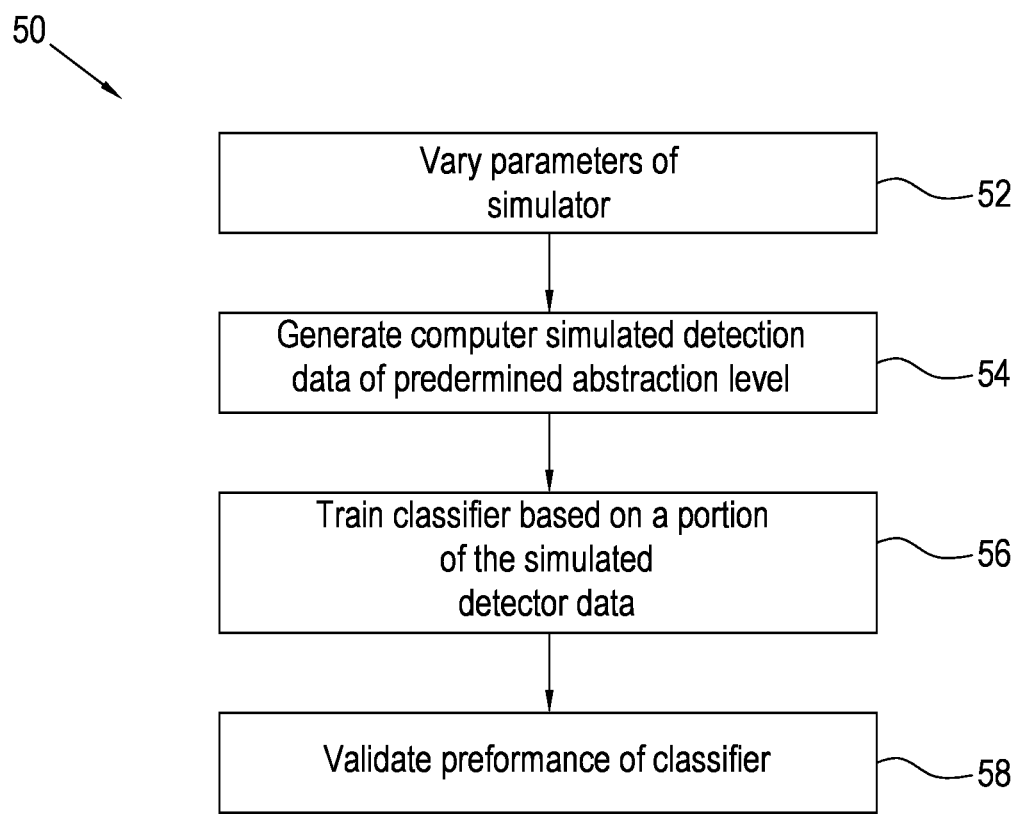
FIG. 9 show another high-level block flow diagram of a method for training a machine-based learning classifier in accordance with an example embodiment of the invention.
Figure 10:
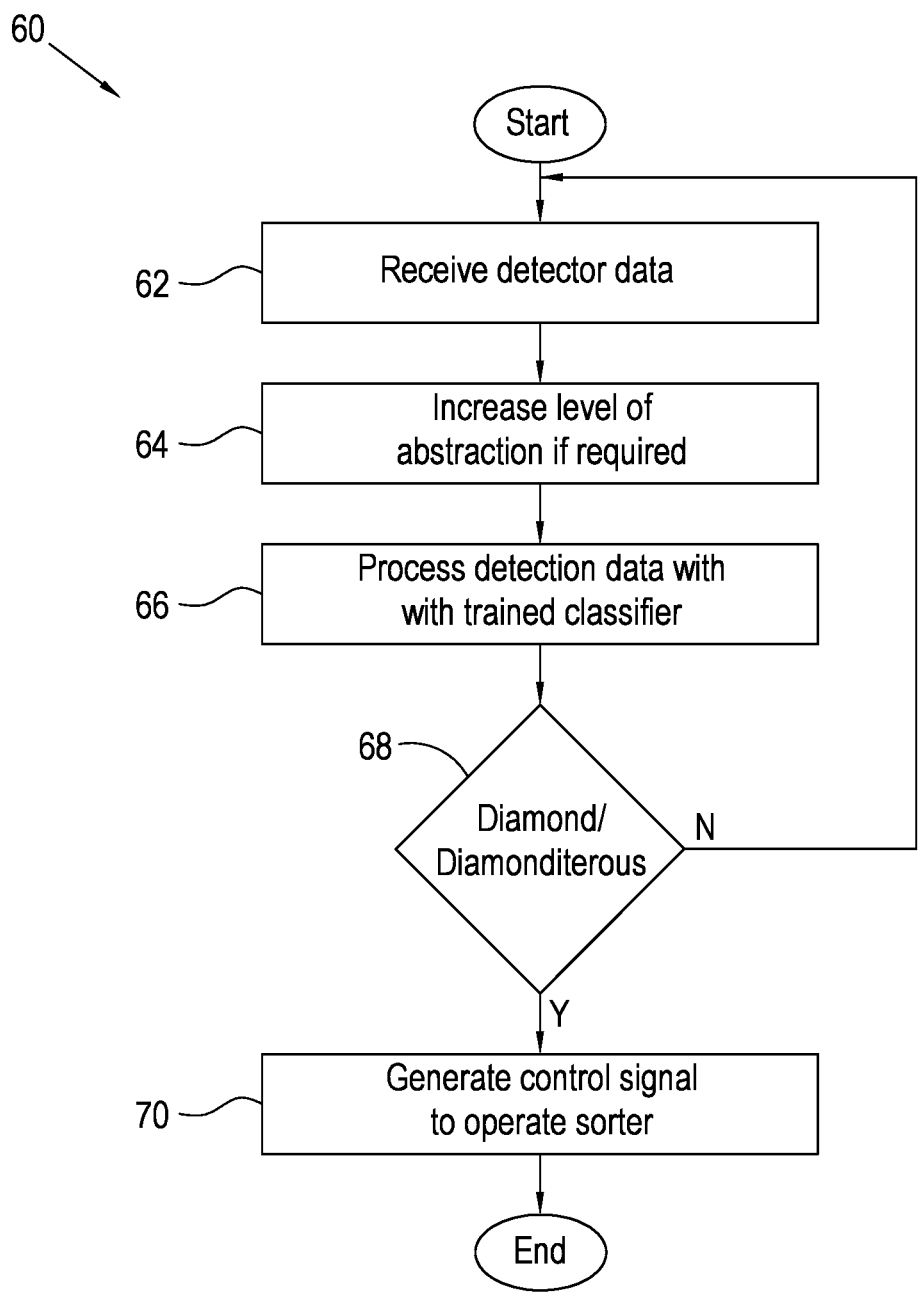
FIG. 10 shows a block flow diagram of a method to detect diamonds in accordance with an example embodiment of the invention.

Referring now to FIGS. 8 to 10 of the drawings where flow diagrams of methods in accordance with example embodiments of the invention is generally indicated by reference numerals 40, 50, 60 respectively. The examples methods 40, 50, 60 may be described, in a non-limiting example, in use with systems of the type described in FIGS. 1 and 2, but nothing precludes the method 40, 50, 60 from being used in other systems not illustrated.

Referring to FIG. 8 of the drawings where the flow diagram of the method 40 is shown. The method 40 typically entails the generation of the computer implemented simulator of a type as herein before described. It will be appreciated that the generation of the computer implemented simulator may be achieved in an offline manner and typically as a prior process.

The method 40 generates a simulator using the Geant4 software as well as Monte Carlo techniques as described above to simulate or provide a simulated model of the physics behind the detection associated with the system for detecting diamonds as herein before described.

The generation of the simulator may entail simulating/modelling various physical parameters associated with diamondiferous rocks with one or more diamonds included in a random fashion within the volume of the rock as well as barren rocks. In addition, the detectors arrangement 22 response as a result of irradiation of the rock with gamma rays as herein before described is also simulated. In other words the simulator simulates/models the entire detection of photons contemplated herein from simulated diamondiferous and barren rocks having been irradiated with gamma rays of the type contemplated herein in the system of FIG. 2, albeit simulated.

The method 40 then includes obtaining experimental data, at block 42, which may be by physically including a diamond in a physical rock and actually subjecting the same to gamma rays of the type described above with reference to FIG. 2 in an effort to detect desired photons also of the type described above of emitted from the diamond by way of a suitable detector arrangement such as arrangement 22. This may be done for many rocks. Physical property data associated with the rocks may be also recorded as part of the experimental data.

The method 40 then comprise benchmarking the generated simulator, to the obtained experimental data, at block 44. This may be achieved by conventional benchmarking techniques which effectively compares the performance of the simulator with the real-world experimental data. To this end, the step of benchmarking may be effectively to validate that the simulator is in fact producing simulations or output data such as computer generated/simulated classification data which corresponds to what one would expect in the real world, at block 46.

If the simulated data does not correspond to experimental data, the similar parameters, or in other words the model details, are tuned and adjusted, at block 48, until the simulator and the simulated data is acceptable.

The validation of the simulator is therefore an important process in that it increases the confidence in the outputs of the simulation which include computer generated classification data for training as described herein.

Referring now to FIG. 9 of the drawings where a block flow diagram of a method 50 is illustrated. The method 50 is generally a method for generating a trained classifier in accordance with an example embodiment of the invention, for example, a classifier as implemented by the processor 30 as described above.

The method 50 comprises varying, at block 52, parameters of the simulator in a random fashion, within predetermined tolerances to avoid errors, and generating computer generated/simulated detection data of a predetermined data abstraction level, at block 54.

As mentioned above, the varying of the parameters of the simulator may be achieved by varying the simulated physical properties of the simulated rocks, properties of the simulated detector arrangement, size and/or grade of diamond inclusions of simulated diamondiferous rocks, locations of the diamond, and the like as will be evident from the preceding discussions. The varying of the parameters of the simulator effectively produce simulated detection data at block 54 of a robust nature as it allows one to have the truth data of which rocks have diamonds and which rocks do not which are verifiable. This is of course starkly different of having to generate data for training of a classify using actual rocks as it is often very difficult to know on real rocks whether or not there are diamonds therein or not. Moreover, it is very difficult and impractical to have to insert diamonds into rocks to serve into different rocks to serve as diamondiferous rocks as contemplated herein.

In particular, in one example embodiment, the computer-generated classification data is in the form of LOR which is then used to reconstruct 3D images as described above. Each image is then divided into blocks of interest where the known diamond positions from the simulator, for example, from Geant4 geometry input files which were used to create blocks containing diamonds.

A number of randomly placed blocks were also created to sample the barren regions of the image. Each diamond containing block was then augmented a number of times by adding a random offset to the block with respect to the original diamond position. This increased the data size for the diamondiferous blocks and made the data set more balanced.

The method 50 comprises the step of separating the computer-generated detection data into a training and validation data set and training the classifier of the type described above with the training data set as being a portion of the computer-generated detected data, at block 56. In one example embodiment, the collection of all blocks made up the training data as described above is fed into the classifier, preferably in the form of a CNN classifier, to train the same.

Once trained, the method 50 comprises the step of validating the performance of the classifier, at block 58, by using the validation data set which is a part of the generated computer-generated detected data. In this way, supervised learning of the classifier is achieved and it may be conveniently determined whether or not a trained classifier is effectively performing, or not.

In the example under discussion, blocks from 3D images of separately simulated rocks with set diamond sizes or diamonds with sizes over a continuous range were used to validate the classifier.

Referring to FIG. 10 of the drawings, a method of detecting diamonds in rocks in a run-of-mine scenario is generally indicated by reference numeral 60. The method 60 may comprise the prior steps of crushing of the rocks into predetermined size by way of a crusher 14 as described above, activating the same by way of an irradiator 16, and holding the irradiated rocks in a hopper 18 for a predetermined period (20-30 minutes as described above) before transporting the same by a suitable conveyor arrangement 20 to the detector arrangement 22.

The irradiated rocks then operatively pass within a detected zone defined by the sensing axes of the detector arrays 22.1, 22.2. Any photons of the type described above which are emitted from the rocks in the back to back fashion described above is detected as a strike//hit by the detector arrangement 22. The detector arrangement 22 is configured to output raw classification data/signals to the system 10 as described herein.

It follows that the method 60 comprises receiving detected data, at block 62, from the detector arrangement 22 in a manner described above.

If necessary, the method 60 may comprise an optionally increasing level of abstraction of the classification data received. This step may be required in instances where the classification data received in step 62 above is of a very low level of data obstruction, for example, raw classification data/signals. The level of abstraction may be increased by way of the manner described above by processing the raw classification data to obtain LoR, then from LoR to a 2D set of 2D projections (forming the 4D sinogram), 3D images using image reconstruction techniques, and then image feature extraction as described above.

The method 60 then comprises processing the detection data received with the trained classifier as described herein. As herein described as length, the trained classifier is conveniently is able to determine whether or not the received detected data corresponds to a diamond and/or diamondiferous rock, or not, at block 68.

If it is determined that the rock under inspection is potentially a diamond/diamondiferous, the method 60 may comprise generating a control signal to operate the sorter 24 at block 70, so as to separate the potentially diamond or diamondiferous rock from barren rocks.

In this regard, though not illustrated, it will be appreciated that the method may comprise tracking rock determined to be potentially diamondiferous and/or loose diamonds and storing data pertaining to its detection in the memory storing device 28. To this end the classifier may, in addition to determining whether or not a rock contains a diamond, also be configured to classify the size and/or grade of a detected diamond/diamond in a rock based on the detected data received thereby. The data pertaining to the detection of a potential diamond may be the location of the diamond/diamondiferous rock on the belt, time of detection, information indicative of the classification of the potential diamond/diamond in diamondiferous rock, location of the potential diamond in the rock, etc.

The data pertaining to the detection of a potential diamond may be useful for directing further crushing for recovery. Moreover, this data may be used for audit purposes where data stored in the device 28 pertaining to the detection of diamonds or diamondiferous rocks may be compared with actual yield from the mine as to be able to curtail and/or mitigate diamond loss through theft, etc.

Figure 11:
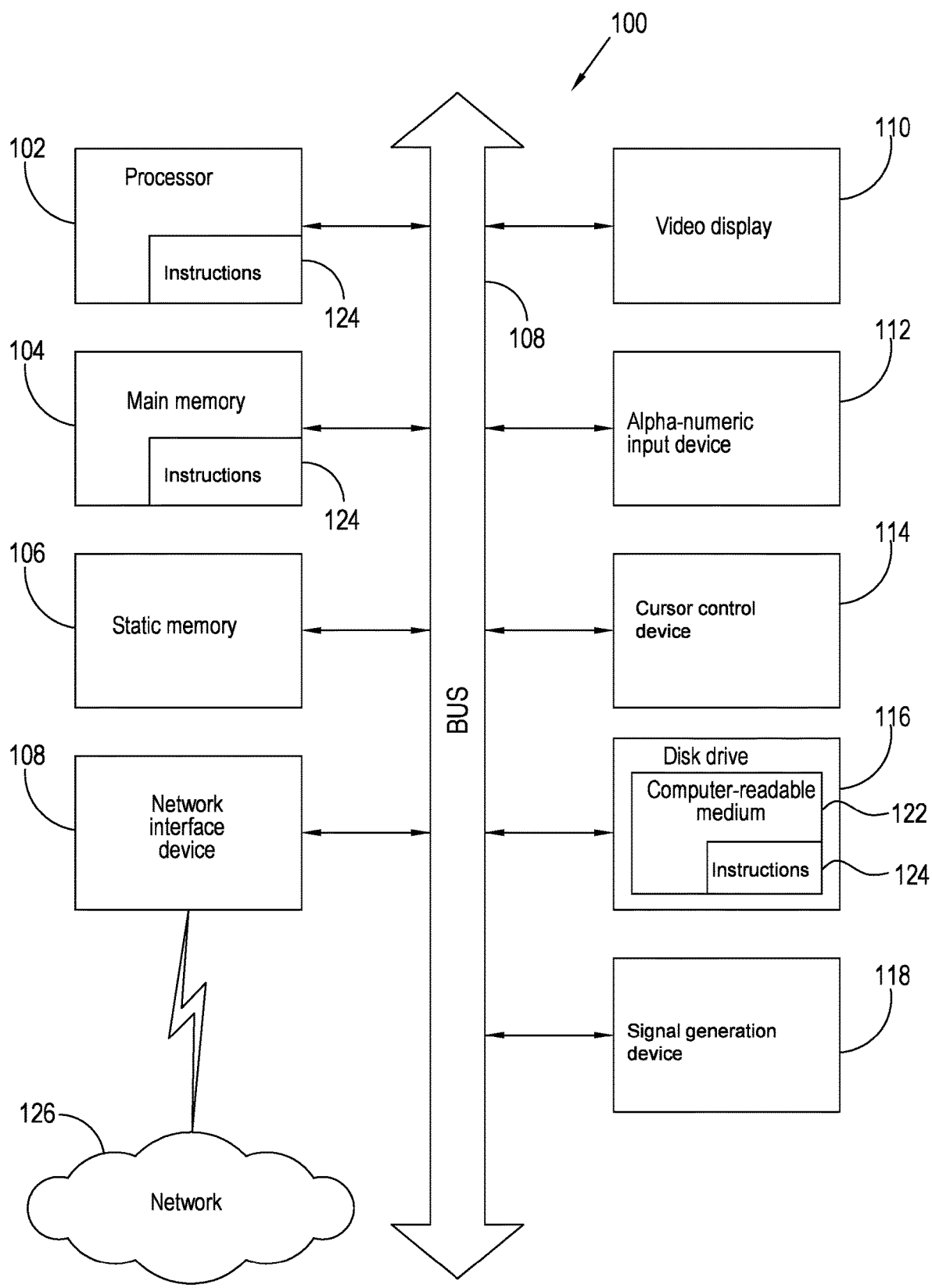
FIG. 11 shows a diagrammatic representation of a machine in the example form of a computer system in which a set of instructions for causing the machine to perform any one or more of the methodologies discussed herein, may be executed.

Referring now to FIG. 11 of the drawings which shows a diagrammatic representation of the machine in the example of a computer system 100 within which a set of instructions, for causing the machine to perform any one or more of the methodologies discussed herein, may be executed. In other example embodiments, the machine operates as a standalone device or may be connected (e.g., networked) to other machines. In a networked example embodiment, the machine may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated for convenience, the term "machine" shall also be taken to include any collection of machines, including virtual machines, that individually or jointly execute a set (or multiple sets) of instructions to perform any one or more of the methodologies discussed herein.

In any event, the example computer system 100 includes a processor 102 (e.g., a central processing unit (CPU), a graphics processing unit (GPU) or both), a main memory 104 and a static memory 106, which communicate with each other via a bus 108. The computer system 100 may further include a video display unit 110 (e.g., a liquid crystal display (LCD) or a cathode ray tube (CRT)). The computer system 100 also includes an alphanumeric input device 112 (e.g., a keyboard), a user interface (UI) navigation device 114 (e.g., a mouse, or touchpad), a disk drive unit 116, a signal generation device 118 (e.g., a speaker) and a network interface device 120.

The disk drive unit 16 includes a non-transitory machine-readable medium 122 storing one or more sets of instructions and data structures (e.g., software 124) embodying or utilised by any one or more of the methodologies or functions described herein. The software 124 may also reside, completely or at least partially, within the main memory 104 and/or within the processor 102 during execution thereof by the computer system 100, the main memory 104 and the processor 102 also constituting machine-readable media.

The software 124 may further be transmitted or received over a network 126 via the network interface device 120 utilising any one of a number of well-known transfer protocols (e.g., HTTP).

Although the machine-readable medium 122 is shown in an example embodiment to be a single medium, the term "machine-readable medium" may refer to a single medium or multiple medium (e.g., a centralized or distributed memory store, and/or associated caches and servers) that store the one or more sets of instructions. The term "machine-readable medium" may also be taken to include any medium that is capable of storing, encoding or carrying a set of instructions for execution by the machine and that cause the machine to perform any one or more of the methodologies of the present invention, or that is capable of storing, encoding or carrying data structures utilised by or associated with such a set of instructions. The term "machine-readable medium" may accordingly be taken to include, but not be limited to, solid-state memories, optical and magnetic media, and carrier wave signals.

Though similar to PET used in medical applications, it will be noted that the techniques described herein rely on source activity distribution which forms via different physical processes. In the present invention, this source activity is embedded in different materials. One has a simpler, higher contrast segmentation. Medical PET has a contrast based on bio-material type and metabolism. Mineral PET has an activation step that creates the PET isotopes and there may be many different PET isotopes which are activated. This occurs according to the description of the input radiation and the cross-section for the induced nuclear reactions for different isotopes present in the rock. Moreover, the present invention entails implementation of dramatically larger detector areas than medical PET, very high data rates, the requirement that the data reconstruction and classification must be completed within seconds, and the result must remain correlated to the moving source stream.

The invention claimed is:

1. A method of detecting presence of diamond in an object, the method comprising:
receiving classification data associated with photons emitted from object as a result of positron annihilation due to irradiation of the object with photons of a predetermined energy at which giant dipole resonance (GDR) occurs due to a nuclear reaction between the photons and carbon, wherein the photons emitted are detected by a suitable detector arrangement; and
determining whether or not the object is potentially a diamond or diamondiferous by processing the received classification data with a trained machine-based learning classifier, wherein the trained machine-based learning classifier is trained at least with computer simulated classification data from a computer implemented simulator which simulates at least diamonds or diamondiferous objects.

2. The method of claim 1, wherein the computer implemented simulator is configured to simulate diamonds or diamondiferous objects and barren objects; and wherein the computer implemented simulator is configured to simulate photon emissions from the simulated objects as a result of simulated positron annihilation due to simulated irradiation of the simulated objects with photons of a predetermined energy at which giant dipole resonance (GDR) occurs due to nuclear reactions between the photons and carbon, wherein the computer simulated classification data is associated with simulated photons emitted from the simulated objects.

3. The method of claim 2, wherein the computer implemented simulator is configured to simulate a detector arrangement configured to detect the simulated photon emissions, wherein the computer simulated classification data comprises simulated output data from the simulated detector arrangement.

4. The method of claim 2, wherein the computer implemented simulator is configured to simulate travelling of simulated objects in a simulated object stream.

5. The method of claim 2, wherein the method comprises prior steps of:
receiving experimental classification data from diamond or diamondiferous test objects and barren test objects;
receiving physical property data corresponding to one or both of quantitative and qualitative aspects of the diamond or diamondiferous test objects and barren test objects; and
using one or both of the received experimental classification data and physical property data to validate the simulations generated by the computer implemented simulator by benchmarking the same to one or both of the received experimental and physical property data.

6. The method of claim 1, wherein the method comprises a prior step of training a machine-based learning classifier with computer simulated classification data generated by the computer implemented simulator to generate the trained machine-based learning classifier which is used to determine whether or not there is a strong likelihood that the object is potentially a diamond or diamondiferous.

7. The method of claim 1, wherein the method comprises:
classifying any potential diamond or diamondiferous object by way of the trained machine-based learning classifier;
storing information indicative of said classification in a memory storage device; and sorting objects based on the classification.

8. The method of claim 1, wherein the method comprises:
irradiating the object with photons of a predetermined energy at which giant dipole resonance (GDR) occurs due to a nuclear reaction between the photons and carbon;
detecting back-to-back co-linear and co-incident gamma ray photons of a predetermined energy level emitted from the irradiated object by way of the detector arrangement, wherein the step of detecting is after a predetermined period of time after the step of irradiating; wherein the method comprises detecting photons having an energy level of approximately 5 11keV and rejecting photons not having the energy level of approximately 5 11keV.

9. The method of claim 1, wherein the method comprises detecting the presence of diamond in an object moving in an object stream within an object sorting system defining a path of travel of objects, wherein the method comprises separating from other objects those objects which are determined potentially to be diamond or diamondiferous in an on-line fashion.

10. A system for detecting presence of diamond in an object, the system comprising:
a memory storage device; and
one or more processors configured to:
receive classification data associated with photons emitted from object as a result of positron annihilation due to irradiation of the object with photons of a predetermined energy at which giant dipole resonance (GDR) occurs due to a nuclear reaction between the photons and carbon, wherein the photons emitted are detected by a suitable detector arrangement; and
determine whether or not the object is potentially a diamond or diamondiferous by processing the received classification data with a trained machine-based learning classifier, wherein the trained machine-based learning classifier is trained at least with computer simulated classification data from a computer implemented simulator which simulates at least diamonds or diamondiferous objects.

11. The system of claim 10, wherein the one or more processors is configured to implement the computer implemented simulator, wherein the computer implemented simulator is configured to simulate diamonds or diamondiferous object, and wherein the computer implemented simulator is configured to simulate photon emissions from the simulated objects as a result of simulated positron annihilation due to simulated irradiation of the simulated objects with photons of a predetermined energy at which giant dipole resonance (GDR) occurs due to nuclear reactions between the photons and carbon, wherein the computer simulated classification data is associated with simulated photons emitted from the simulated objects.

12. The system of claim 10, wherein the system comprises a sorter configured to sort objects which are diamonds or diamondiferous from those that are barren.

13. The system of claim 10, wherein the one or more processors is configured to classify any potential diamond or diamondiferous object by way of the trained machine-based learning classifier; and store information indicative of said classification in the memory storage device.

14. The system of claim 10, wherein the system comprises the detector arrangement; and wherein the detector arrangement comprises a pair of detector arrays oriented parallel to each other and having sensing axes transverse to the direction of travel of the belt.

15. The system of claim 10, wherein the system comprises an irradiator configured to irradiate the object with photons of a predetermined energy at which giant dipole resonance (GDR) occurs due to a nuclear reaction between the photons and carbon, wherein the detector arrangement is configured to detecting back-to-back co-linear and co-incident gamma ray photons of a predetermined energy level emitted from the irradiated object by way of the detector arrangement.

16. A method for auditing output from a diamond mine, wherein the method comprises:
detecting, at a diamond mine, presence of diamond in an object according to the method as claimed in claim 1;
storing data associated with objects determined to be potentially a diamond or diamondiferous; and comparing the stored data with yield data from the diamond mine indicative of the yield of diamonds from the diamond mine.

17. A system for auditing output from a diamond mine, wherein the system comprises:
a memory storage device; and
one or more processors configured to:
detect presence of diamond in an object using the system as claimed in claim 10;
storing data associated with objects determined to be potentially a diamond or diamondiferous; and
comparing the stored data with yield data from the diamond mine indicative of the yield of diamonds from the diamond mine.

18. A non-transitory computer-readable medium storing computer executable instructions which when executed on one or more processors cause said processors to:
receive classification data associated with photons emitted from object as a result of positron annihilation due to irradiation of the object with photons of a predetermined energy at which giant dipole resonance (GDR) occurs due to a nuclear reaction between the photons and carbon, wherein the photons emitted are detected by a suitable detector arrangement; and determine whether or not the object is potentially a diamond or diamondiferous by processing the received classification data with a trained machine-based learning classifier.

19. A method of training a machine-based learning classifier, wherein the method comprises training the machine-based learning classifier with computer simulated classification data generated by a computer implemented simulator which simulates at least diamonds or diamondiferous objects thereby to generate a trained machine-based learning classifier which is used to determine whether or not there is a strong likelihood that the object is potentially a diamond or diamondiferous.

20. A system for training a machine-based learning classifier, wherein the system comprises:

a memory storage device; and one or more processors configured to:

train a machine-based learning classifier with computer simulated classification data generated by the computer implemented simulator to generate a trained machine-based learning classifier as defined in claim 10 which is used to determine whether or not there is a strong likelihood that the object is potentially a diamond or diamondiferous.

\* \* \* \* \*